United States Patent

Jegham et al.

[11] Patent Number: 5,925,662
[45] Date of Patent: Jul. 20, 1999

[54] COMPOUNDS DERIVED FROM OXAZOLIDIN-2-ONE AND PREPARATION AND THERAPEUTICAL USE THEREOF

[75] Inventors: Samir Jegham, Argenteuil; Frederic Puech, Rueil Malmaison; Philippe Burnier, Maisons Laffitte; Danielle Berthon, Mareil Marly, all of France

[73] Assignee: Synthelabo, Le Plessis Robinson, France

[21] Appl. No.: 09/066,364

[22] PCT Filed: Nov. 5, 1996

[86] PCT No.: PCT/FR96/01732

§ 371 Date: May 8, 1998

§ 102(e) Date: May 8, 1998

[87] PCT Pub. No.: WO97/17347

PCT Pub. Date: May 15, 1997

[30] Foreign Application Priority Data

Nov. 9, 1995 [FR] France .................................. 95 13257

[51] Int. Cl.$^6$ ...................... C07D 413/04; A61K 31/42
[52] U.S. Cl. .......................... 514/376; 548/232; 549/404; 549/462
[58] Field of Search ............................... 548/232; 514/376

[56] References Cited

U.S. PATENT DOCUMENTS

| 4,259,338 | 3/1981 | Paioni et al. | 424/267 |
| 4,517,197 | 5/1985 | Ancher et al. | 514/376 |
| 5,036,090 | 7/1991 | Jarreau et al. | 514/376 |
| 5,036,091 | 7/1991 | Jarreau et al. | 514/376 |
| 5,171,747 | 12/1992 | Jarreau et al. | 514/376 |
| 5,196,543 | 3/1993 | Jarreau et al. | 548/232 |
| 5,235,063 | 8/1993 | Jarreau et al. | 548/232 |

FOREIGN PATENT DOCUMENTS 8-151577  6/1996  Japan .

*Primary Examiner*—Mark L. Berch
*Assistant Examiner*—Ann Razgunas
*Attorney, Agent, or Firm*—Jacobson, Price, Holman & Stern, PLLC

[57] ABSTRACT

Derivatives of oxazolidin-2-one of general formula (I)

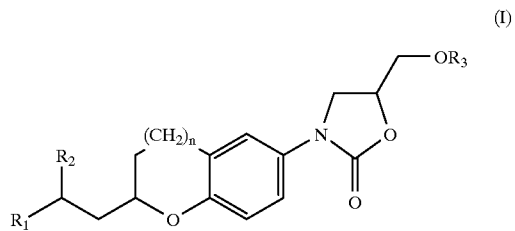

in which:

n is equal to 0 or 1, $R_1$ represents a cyano group, an alkyl group or a fluoroalkyl group, $R_2$ represents a hydrogen atom or a hydroxyl group, and $R_3$ represents a hydrogen atom or a methyl group.

Application in therapeutics.

9 Claims, No Drawings

COMPOUNDS DERIVED FROM OXAZOLIDIN-2-ONE AND PREPARATION AND THERAPEUTICAL USE THEREOF

The present invention relates to compounds derived from oxazolidin-2-one, a process for their preparation and their application in therapeutics.

The compounds of the invention correspond to the general formula (I)

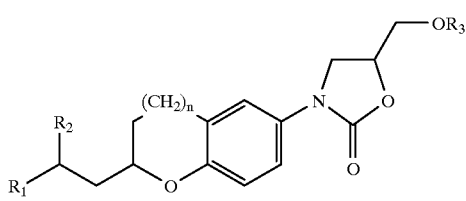

in which:
n is equal to 0 or 1,
R$_1$ represents a cyano group, an alkyl group comprising 1 to 4 carbon atoms or a fluoroalkyl group comprising 1 to 4 carbon atoms,
R$_2$ represents a hydrogen atom or a hydroxyl group, and
R$_3$ represents a hydrogen atom or a methyl group.
In the context of the present invention:
an alkyl group is an aliphatic, saturated, linear or branched group,
a fluoroalkyl group is an alkyl group such as defined above, of which at least one of the carbon atoms is substituted by one or more fluorine atoms. Usually, a fluoroalkyl group according to the invention comprises 3 fluorine atoms substituted onto the terminal carbon atom of the alkyl chain.

Preferred compounds of formula (I) are those for which (i) R$_1$ represents a cyano, methyl or trifluoromethyl group and/or (ii) R$_3$ represents a methyl group.

The compounds of formula (I) have at least two asymmetric carbon atoms, one in position 5 of the oxazolidine, the other in position 2 of the dihydrobenzofuran or of the dihydrobenzopyran (these positions are respectively indicated by 5 and 2 in the configurations). They can thus exist in the form of enantiomers or of diastereoisomers. The invention comprises these different forms as well as their mixtures, including their racemic mixtures.

The compounds of formula (I) can be prepared according to the process represented in Annex 1. The compounds of formula (I) in which R$_3$ represents a methyl group can be prepared starting from a compound of formula (II)

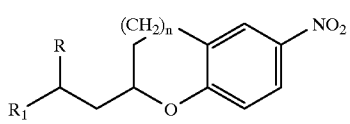

in which n and R$_1$ are defined as in formula (I) and R is a hydrogen atom or an OR' group, in which R' represents a hydroxy protective group such as the phenylmethyl group (Bn).

According to this process, the nitro group of the compound of formula (II) is reduced and the compound of formula (III)

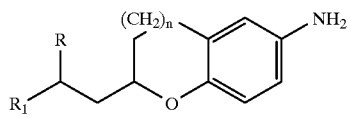

prepared in this way is reacted with ethyl chloroformate and sodium bicarbonate to obtain a compound of formula (IV)

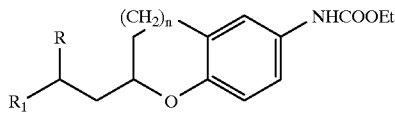

where R, R$_1$ and n have the meanings indicated above and Et is an ethyl group.

The compound of formula (IV) can then be reacted with 4-methoxymethyl-1,3-dioxolan-2-one to obtain either a compound of formula (I) in which R$_2$ is a hydrogen atom and R$_3$ is a methyl group, or a compound of formula (V)

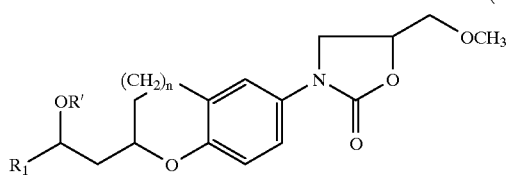

where R$_1$, R' and n have the meanings indicated further above, which is deprotected to give a compound of formula (I) in which R$_2$ represents a hydroxyl group, and optionally treated with thiocarbonyldiimidazole (TCDI), then with tributyltin hydride and α,α'-azodiisobutyronitrile (AIBN) to give a compound of formula (I) in which R$_2$ represents a hydrogen atom.

The compounds of formula (I) where R$_3$ represents a hydrogen atom can be prepared, starting from corresponding compounds of formula (I) where R$_3$ represents a methyl group, by reaction with boron tribromide.

The compounds of formula (I) in which R$_2$ represents a hydrogen atom and n is equal to 0, can likewise be prepared according to the process represented in Annex 2, by reduction of the corresponding benzofuran derivative of formula (IX)

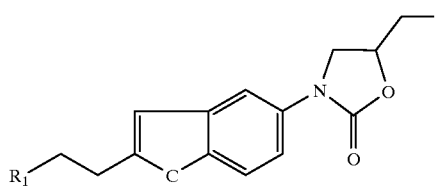

in which R$_1$ is defined as previously. The reduction can be carried out, for example, by hydrogen in the presence of a catalyst such as palladium on carbon.

The compounds of formula (IX) can be prepared starting from (2-hydroxy-5-nitrophenyl) methyltriphenylphosphonium bromide (compound described in Chem. Ber. 1986, 119, 2169), which is reacted with an acid chloride of formula $R_1(CH_2)_2COCl$, where $R_1$ has one of the meanings indicated in formula (I), to prepare a 5-nitrobenzofuran derivative of formula (VI)

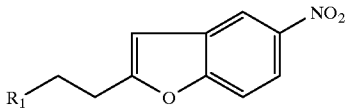
(VI)

which is then treated to form a 5-aminobenzofuran derivative of formula (VII)

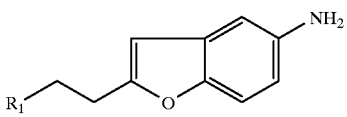
(VII)

which is then in turn treated to form 5-ethoxycarbonylaminobenzofuran of formula (VIII)

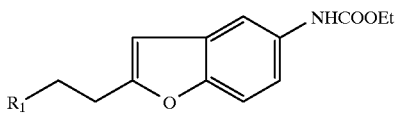
(VIII)

which is then reacted with 4-methoxymethyl-1,3-dioxolan-2-one according to a procedure analogous to the procedure described previously. In the compounds of formula (VI), (VII) and (VIII), $R_1$ has one of the meanings given for the formula (I).

The compounds of formula (II) in which $R_1$ represents a cyano or trifluoromethyl group and R represents a hydrogen atom or else in which $R_1$ represents a trifluoromethyl group and R represents a phenylmethoxy group can be prepared according to one of the processes represented in Annex 3.

According to one of these processes, compounds of formula (II) in which $R_1$ is a cyano group and R is a hydrogen atom, that is to say compounds of formula (IIa)

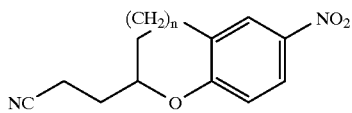
(IIa)

are prepared by reacting a compound of formula (X)

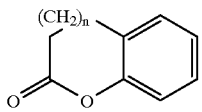
(X)

in which n is defined as in formula (I), with carbethoxymethyltriphenylphosphorane to prepare a compound of formula (XI)

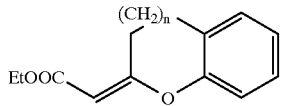
(XI)

which can then be reduced, for example by hydrogen in the presence of a catalyst such as palladium on carbon, to prepare a compound of formula (XII)

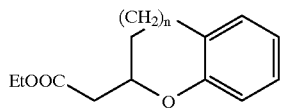
(XII)

which can in turn be treated with lithium aluminum hydride ($LiAlH_4$) to prepare a compound of formula (XIII)

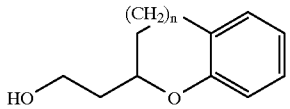
(XIII)

which can itself be treated with p-toluenesulfonyl chloride (TsCl or tosyl chloride) to form a compound of formula (XIV)

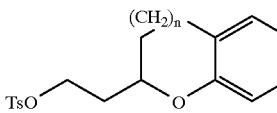
(XIV)

where Ts represents a p-toluenesulfonyl group. The compound of formula (XIV) can then be treated with potassium cyanide to prepare a compound of formula (XV)

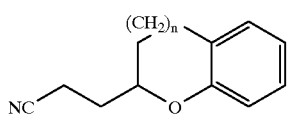
(XV)

which is then in turn treated with sodium nitrate to lead to the desired compound of formula (IIa).

According to another process described in Annex 3, compounds of formula (II) in which $R_1$ is a trifluoromethyl group and R is a phenylmethoxy group, that is to say compounds of formula (IIb)

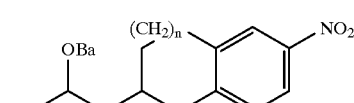
(IIb)

can be prepared by reacting a compound of formula (XIII), obtained by the process described previously, with pyridinium chlorochromate (PCC) to prepare a compound of formula (XVII)

(XVII)

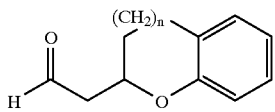

which is then treated with trifluorotrimethylsilylmethane (F₃CTMS), in the presence of tetrabutylammonium fluoride (TBAF), to form a compound of formula (XVIII)

(XVIII)

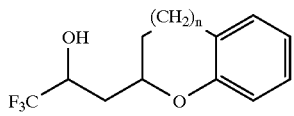

which is then reacted with sodium nitrate to prepare a compound of formula (XIX)

(XIX)

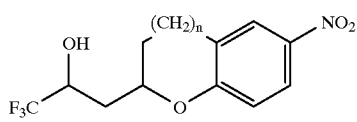

The compound of formula (XIX) is then reacted with phenylmethyl bromide to lead to the desired compound of formula (IIb).

The compounds of formula (XVII) mentioned above can likewise be prepared either starting from a compound of formula (XVI)

(XVI)

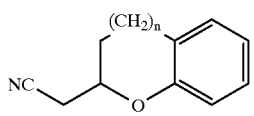

by reaction with diisobutylaluminum hydride and acidic hydrolysis, or starting from a compound of formula (XX)

(XX)

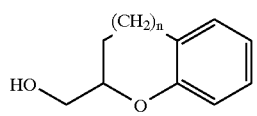

by reaction with triflic anhydride, in the presence of pyridine, to prepare a compound of formula (XXI)

(XXI)

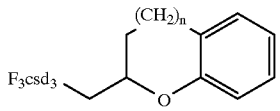

which can then be treated with cuprous bromide-dimethyl sulfide and vinylmagnesium bromide to form a compound of formula (XXII)

(XXII)

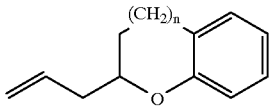

which can then be in turn treated with ozone, then dimethyl sulfide, to obtain said compound of formula (XVII).

According to yet another process described in Annex 3, compounds of formula (II) in which $R_1$ is a trifluoromethyl group and R is a hydrogen atom, that is to say compounds of formula (IIc)

(IIc)

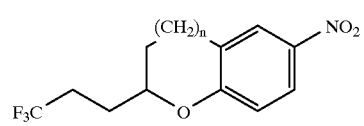

can be prepared by treating a compound of formula (XVIII), obtained by the process described previously, with thiocarbonyldiimidazole and then with tributyltin and α,α'-azodiisobutyronitrile, so as to prepare a compound of formula (XXIII)

(XXIII)

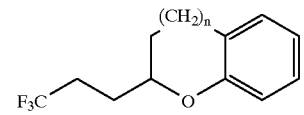

which is then treated with sodium nitrate.

The compound of formula (II) in which $R_1$ represents an alkyl group comprising 1 to 4 carbon atoms or a fluoroalkyl group comprising 1 to 4 carbon atoms, R represents a hydrogen atom and n is equal to 1, that is to say a compound of formula (IId), can be prepared according to the process represented in Annex 4, according to which 2-hydroxyacetophenone

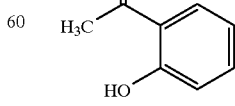

is reacted with an acid chloride of formula $R_1CH_2CH_2COCl$, where $R_1$ represents an alkyl group comprising 1 to 4 carbon atoms or a fluoroalkyl group comprising 1 to 4 carbon atoms, so as to prepare a compound of formula (XXIV)

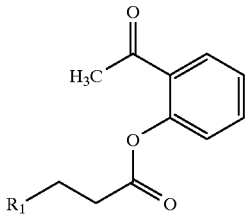
(XXIV)

which is treated with potassium hydroxide to form a compound of formula (XXV)

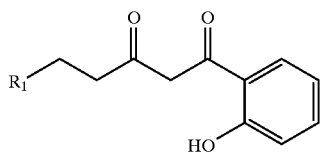
(XXV)

which is treated with hydrochloric acid to form a compound (XXVI)

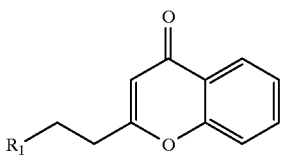
(XXVI)

which can be reduced by hydrogen in the presence of a catalyst to prepare a compound (XXVII)

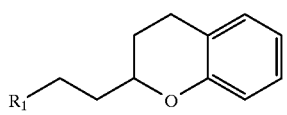
(XXVII)

which is treated with sodium nitrate to lead to the desired compound of formula (IId).

The 5(R) and 5(S) isomers of the compounds of formula (I) can be prepared by reaction of a compound of formula (IV) described above with the 4(S) and 4(R) isomers of 4-methoxymethyl-1,3-dioxolan-2-one respectively.

4(S)-Methoxymethyl-1,3-dioxolan-2-one is a known compound whose preparation is described in the Patent EP-0 511 031.

4(R)-Methoxymethyl-1,3-dioxolan-2-one is prepared according to the same method, starting from (R)-2,2-dimethyl-1,3-dioxolan-4-methanol.

The compounds of formula (I) can exist in the form of (R) and (S) enantiomers in position 2 of the dihydrobenzopyran or dihydrobenzofuran group. These enantiomers are prepared starting from 2(R) and 2(S) enantiomers of the compounds of formula (II).

The enantiomers of the compounds of formula (IIb) and (IIc) can be obtained starting from 2(R) and 2(S) enantiomers of the compounds of formula (XVII), themselves obtained, starting from 2(R) and 2(S) enantiomers of the compounds of formula (XX), according to the process represented in Annex 3. The enantiomers of the compounds of formula (XX) can be obtained according to the process described in the Patent Application EP-A-0 546 388.

The following examples illustrate the present invention.

EXAMPLE 1

3-[2-(2-hydroxy-3,3,3-trifluoropropyl)-3,4-dihydro-2H-1-benzopyran-6-yl]-5(R)-methoxymethyloxazolidin-2-one 1.1. 3,4-Dihydro-2H-1-benzopyran-2-acetaldehyde To a solution of 8.3 g (48 mmol) of 3,4-dihydro-2H-1-benzopyran-2-acetonitrile (compound described in the Patent EP 0252005) in 58 ml (58 mmol) of dichloromethane are added dropwise, at −50° C., 58 ml of a 1M solution of diisobutylaluminum hydride. The mixture is stirred for 30 min while allowing the temperature to rise from −50° C. to 0° C., and then the mixture is hydrolyzed with a 1M solution of hydrochloric acid and the product is extracted with dichloromethane. The organic phase is washed with water, dried over sodium sulfate and then concentrated under reduced pressure. By chromatography of the residue on a silica column using dichloromethane, 6.9 g of product are obtained in oil form.

1.2. 2-(2-Hydroxy-3,3,3-trifluoropropyl)-3,4-dihydro-2H-1-benzopyran

To a solution of 7.6 g (43 mmol) of 3,4-dihydro-2H-1-benzopyran-2-acetaldehyde in 110 ml of tetrahydrofuran are added dropwise, at −10° C., 7.1 ml (52 mmol) of trifluorotrimethylsilylmethane and a solution of 90 mg (2 mg/mmol) of tetrabutylammonium fluoride in 5 ml of tetrahydrofuran. The mixture is allowed to react for 2 hours at 0° C., then it is hydrolyzed for 2 hours using a 1M solution of hydrochloric acid and the product is extracted with diethyl ether. The organic phase is then washed with water, dried over sodium sulfate and then concentrated under reduced pressure. By chromatography of the residue on a silica column using a 50/50 mixture of dichloromethane and of cyclohexane, 8.6 g of product are obtained in oil form.

1.3. 2-(2-Hydroxy-3,3,3-trifluoropropyl)-6-nitro-3,4-dihydro-2H-1-benzopyran

A solution of 8.5 g (35 mmol) of 2-(2-hydroxy-3,3,3-trifluoropropyl)-3,4-dihydro-2H-1-benzopyran in 106 ml of trifluoroacetic acid is treated with 7.4 g (88 mmol) of sodium nitrate at −10° C. The mixture is allowed to react for 45 min, then poured into ice water and the product is extracted with dichloromethane. The organic phase is then dried over sodium sulfate and concentrated under reduced pressure. By chromatography of the residue on a silica column using dichloromethane, 5.0 g of product are obtained.

1.4. 2-(2-Phenylmethoxy-3,3,3-trifluoropropyl)-6-nitro-3,4-dihydro-2H-1-benzopyran A solution of 5.0 g (17 mmol) of 2-(2-hydroxy-3,3,3-trifluoropropyl)-6-nitro-3,4-dihydro-2H-1-benzopyran in a mixture of 60 ml of toluene and 20 ml of dichloromethane is stirred for 3 hours with 6.1 ml (52 mmol) of benzyl bromide, 0.55 g (1.7 mmol) of tetrabutylammonium bromide and a solution of 2.7 g (69 mmol) of sodium hydroxide in 5.4 ml of water. The reaction mixture is then diluted with dichloromethane and washed with water, then the organic phase is dried over sodium sulfate and concentrated under reduced pressure. By chromatography of the residue on a silica column using cyclohexane containing 0 to 50% of dichloromethane, 5.9 g of product are obtained.

1.5. 2-(2-Phenylmethoxy-3,3,3-trifluoropropyl)-6-amino-3,4-dihydro-2H-1-benzopyran To a solution of 5.9 g (16 mmol) of 2-(2-phenylmethoxy-3,3,3-trifluoropropyl)-6-nitro-3,4-dihydro-2H-1-benzopyran in 50 ml of dichloromethane and 25 ml of water are added 73 mg of Adogen 464, 660 mg of 5% palladium on carbon containing 50% of water, and then a solution of 1.1 g (28 mmol) of sodium borohydride in 10 ml of water. The mixture is stirred for 1 hour, then it is filtered and the product is extracted with dichloromethane. The organic phase is dried over sodium sulfate and concentrated under reduced pressure. By chromatography of the residue on a silica column using dichloromethane, 5.4 g of product are obtained.

1.6. 2-(2-Phenylmethoxy-3,3,3-trifluoropropyl)-6-ethoxycarbonylamino-3,4-dihydro-2H-1-benzopyran A solution of 3.6 g (10 mmol) of 2-(2-phenylmethoxy-3,3,3-trifluoropropyl)-6-amino-3,4-dihydro-2H-1-benzopyran in 34 ml of a 9/1 mixture of tetrahydrofuran and water is reacted for 20 min with 1.1 ml (11 mmol) of ethyl chloroformate and 1.3 g (15 mmol) of sodium hydrogencarbonate. The mixture is then diluted with water and the product is extracted with dichloromethane. The organic phase is dried over sodium sulfate and concentrated under reduced pressure. By chromatography of the residue on a silica column using a 20/80 mixture of cyclohexane and dichloromethane, 4.2 g of product are obtained.

1.7. 3-[2-(2-Phenylmethoxy-3,3,3-trifluoropropyl)-3,4-dihydro-2H-1-benzopyran-6-yl]-5(R)-methoxymethyloxazolidin-2-one A solution of 4.2 g (9.9 mmol) of 2-(2-phenylmethoxy-3,3,3-trifluoropropyl)-6-ethoxycarbonylamino-3,4-dihydro-2H-1-benzopyran in 40 ml of dimethylformamide is stirred for 24 hours, at 130° C., in the presence of 140 mg (1.0 mmol) of potassium carbonate and of 3.4 g (26 mmol) of 4(S)-methoxymethyl-1,3-dioxolan-2-one added in 3 hours. The mixture is cooled, diluted with water and the product is extracted with diethyl ether. The organic phase is then dried over sodium sulfate, concentrated under reduced pressure and chromatographed on a silica column using a 30/70 mixture of ethyl acetate and cyclohexane. The product obtained is used as such in the following step.

1.8. 3-[2-(2-Hydroxy-3,3,3-trifluoropropyl)-3,4-dihydro-2H-1-benzopyran-6-yl]-5(R)-methoxymethyloxazolidin-2-one 3-[2-(2-phenylmethoxy-3,3,3-trifluoropropyl)-3,4-dihydro-2H-1-benzopyran-6-yl]-5(R)-methoxymethyloxazolidin-2-one obtained in the preceding step is hydrogenated for 18 hours in 80 ml of ethanol, in the presence of 1.0 g of 5% palladium on carbon containing 50% of water and 0.5 ml of hydrochloric ethanol. The mixture is then filtered, concentrated under reduced pressure and chromatographed several times on a silica column using a 1% mixture of methanol in dichloromethane. After recrystallization in diisopropyl ether, there are obtained:

- 1.2 g of the mixture of the two least polar diastereoisomers (mixture 1a). Melting point: 133–134° C.,
- 1.2 g of the mixture of the two most polar diastereoisomers (mixture 1b). Melting point: 81–83° C., and
- 0.5 g of the mixture of the four diastereoisomers (mixture 1c).

EXAMPLE 2

3-[2-(2-hydroxy-3,3,3-trifluoropropyl)-3,4-dihydro-2H-1-benzopyran-6-yl]-5(R)-hydroxymethyloxazolidin-2-one To a solution of 0.40 g (1.1 mmol) of the mixture 1b of diastereoisomers obtained in step 8 of Example 1 in 15 ml of dichloromethane is added dropwise, at −5° C., a solution of 3.0 ml (3.0 mmol) of a 1M solution of boron tribromide in dichloromethane. The mixture is stirred at 0° C. for 45 min, then hydrolyzed by adding ammonia until the pH is basic. The product is then extracted with dichloromethane, and the organic phase is washed with water, dried over sodium sulfate and concentrated under reduced pressure. By chromatography of the residue on a silica column using a 2% solution of methanol in dichloromethane, then trituration of the product obtained in a mixture of petroleum ether and diisopropyl ether, 0.18 g of product is obtained.

Melting point: 123.7–123.8° C. $[\alpha]_D^{20}$=−31.8° (c=1; dimethyl sulfoxide).

EXAMPLE 3

3-[2-(3,3,3-trifluoropropyl)-3,4-dihydro-2H-1-benzopyran-6-yl]-5(R)-methoxymethyloxazolidin-2-one 620 mg (1.7 mmol) of the mixture 1a of diastereoisomers obtained in step 8 of Example 1 is reacted at reflux for 6 hours in solution in 15 ml of dichloroethane with 510 mg (2.9 mmol) of thiocarbonyldiimidazole. The mixture is then diluted with dichloromethane and washed with water. The organic phase is dried over sodium sulfate and then concentrated under reduced pressure and coevaporated with toluene. The oil obtained is dissolved in 60 ml of toluene, deaerated, and then heated to reflux under argon. 670 µl (2.5 mmol) of tributyltin hydride and 11 mg (0.07 mmol) of α,α'-azoisobutyronitrile are then added, the mixture is heated for 30 min, and the solvent is evaporated under reduced pressure. Hexane and acetonitrile are added to the oil obtained, then the acetonitrile phase is separated and concentrated under reduced pressure. By chromatography of the residue on a silica column using a 0–30% mixture of ethyl acetate in cyclohexane and recrystallization in diisopropyl ether, 220 mg of product are obtained.

Melting point: 110–111° C.

EXAMPLE 4

3-[2(S)-(3,3,3-trifluoropropyl)-3,4-dihydro-2H-1-benzopyran-6-yl]-5(R)-methoxymethyloxazolidin-2-one and 3-[2(R)-(3,3,3-trifluoropropyl)-3,4-dihydro-2H-1-benzopyran-6-yl]-5(R)-methoxymethyloxazolidin-2-one

4.1. 2(S)-Trifluoromethylsulfonyloxymethyl-3,4-dihydro-2H-1-benzopyran

To a solution of 64.8 g (395 mmol) of 2(S)-hydroxymethyl-3,4-dihydro-1-benzopyran (compound described in the Patent EP 546388) and 75 ml (927 mmol) of pyridine in 800 ml of dichloromethane is added dropwise, at −10° C., a solution of 80 ml (470 mmol) of triflic anhydride in 200 ml of dichloromethane. The mixture is stirred for 15 min at 0° C., then hydrolyzed with a 1M solution of hydrochloric acid. The product is extracted with dichloromethane, and the organic phase is washed with an aqueous solution of sodium hydrogencarbonate and then water, dried over sodium sulfate and concentrated under reduced pressure. By chromatography of the residue on a silica column using dichloromethane, 100 g of product are obtained in oil form.

$[\alpha]_D^{20}$=+67.1° (c=1; methanol).

4.2. 2(S)-Propenyl-3,4-dihydro-2H-1-benzopyran

To a mixture of 100 g (338 mmol) of 2(S)-trifluoromethylsulfonyloxymethyl-3,4-dihydro-2H-1-benzopyran and 12 g (58 mmol) of cuprous bromide/ dimethyl sulfide in 400 ml of tetrahydrofuran are added dropwise, at −5° C., 1000 ml of a 1M solution of vinylmagnesium bromide. The mixture is stirred for 2 hours at 0° C., then hydrolyzed with a solution of ammonium chloride. The product is then extracted with ethyl acetate, and the organic phase is washed with water, dried over sodium sulfate and concentrated under reduced pressure. By chromatography of the residue on a silica column using cyclohexane, 29 g of product are obtained in oil form.

$[\alpha]_D^{20}$=+120.10° (c=1; methanol).

According to the same process, starting from 84 g (284 mmol) of 2(R)-trifluoromethylsulfonyloxymethyl-3,4-dihydro-2H-1-benzopyran (compound described in J. Heterocycl. Chem. 1992, 29, 431–438), 20.3 g of 2(R)-propenyl-3,4-dihydro-2H-1-benzopyran were obtained in oil form.

$[\alpha]_D^{20}$=−122.0° (c=1; methanol).

4.3. 2(S)-3,4-Dihydro-2H-1-benzopyran-2-acetaldehyde

A stream of ozone is passed at −40° C., for 6 hours, into a solution of 29 g (167 mmol) of 2(S)-propenyl-3,4-dihydro-2H-1-benzopyran in 900 ml of dichloromethane. The excess of ozone is then expelled by bubbling in argon and 122 ml (1.7 mol) of dimethyl sulfide are added. The mixture is stirred at ambient temperature for 2 days, then the solvent is evaporated under reduced pressure. By chromatography of the residue on a silica column using a 10% mixture of ethyl acetate in cyclohexane, 15.3 g of product are obtained in oil form.

$[\alpha]_D^{20}$=+73.3° (c=1; dichloromethane).

According to the same process, starting from 20 g (115 mmol) of 2(R)-propenyl-3,4-dihydro-2H-1-benzopyran, 11.8 g of 2(R)-3,4-dihydro-2H-1-benzopyran-2-acetaldehyde were obtained in oil form.

$[\alpha]_D^{20}$=−95.4° (c=1; dichloromethane).

4.4. 2(S)-2-(2-Hydroxy-3,3,3-trifluoropropyl)-3,4-dihydro-2H-1-benzopyran 15.3 g (87 mmol) of 2(S)-3,4-dihydro-2H-1-benzopyran-2-acetaldehyde are treated under the conditions described in step 2 of Example 1. 14.2 g of product are obtained in oil form.

$[\alpha]_D^{20}$=+72.9° (c=1; dichloromethane).

According to the same process, starting from 11.8 g (67 mmol) of 2(R)-3,4-dihydro-2H-1-benzopyran-2-acetaldehyde, 11.3 g of 2(R)-(2-hydroxy-3,3,3-trifluoropropyl)-3,4-dihydro-2H-1-benzopyran were obtained in oil form.

$[\alpha]_D^{20}$=−87.2° (c=1, dichloromethane).

4.5. 2(S)-(3,3,3-Trifluoropropyl)-3,4-dihydro-2H-1-benzopyran 14.1 g (57.3 mmol) of 2(S)-(2-hydroxy-3,3,3-trifluoropropyl)-3,4-dihydro-2H-1-benzopyran are treated under conditions analogous to those of Example 3. 8.5 g of product are obtained in oil form.

$[\alpha]_D^{20}$=+78.7° (c=1; dichloromethane).

According to the same process, starting from 11.2 g (46 mmol) of 2(R)-(2-hydroxy-3,3,3-trifluoropropyl)-3,4-dihydro-2H-1-benzopyran, 5.9 g of 2(R)-(3,3,3-trifluoropropyl)-3,4-dihydro-2H-1-benzopyran were obtained in oil form.

$[\alpha]_D^{20}$=−92.2° (c=1; dichloromethane).

4.6. 6-Nitro-2(S)-(3,3,3-trifluoropropyl)-3,4-dihydro-2H-1-benzopyran 10.1 g (44 mmol) of 2(S)-(3,3,3-trifluoropropyl)-3,4-dihydro-2H-1-benzopyran are treated under the conditions described in step 3 of Example 1. 6.0 g of product are obtained in oil form.

According to the same process, starting from 7.6 g (33 mmol) of 2(R)-(3,3,3-trifluoropropyl)-3,4-dihydro-2H-1-benzopyran, 4.6 g of 6-nitro-2(R)-(3,3,3-trifluoropropyl)-3,4-dihydro-2H-1-benzopyran were obtained.

4.7. 6-Amino-2(S)-(3,3,3-trifluoropropyl)-3,4-dihydro-2H-1-benzopyran

A solution of 6.0 g (22 mmol) of 6-nitro-2(S)-(3,3,3-trifluoropropyl)-3,4-dihydro-2H-1-benzopyran are hydrogenated in 50 ml of tetrahydrofuran and 65 ml of methanol, in the presence of 0.6 g of 10% palladium on carbon containing 50% of water. The mixture is stirred for 18 hours, then filtered and the filtrate is concentrated under reduced pressure. By chromatography of the residue on a silica column using a 30% mixture of ethyl acetate in cyclohexane, 3.4 g of product are obtained in oil form.

$[\alpha]_D^{20}$=+76.8° (c=1; dichloromethane).

According to the same process, starting from 4.6 g (16.7 mmol) of 6-nitro-2(R)-(3,3,3-trifluoropropyl)-3,4-dihydro-2H-1-benzopyran, 2.5 g of 6-amino-2(R)-(3,3,3-trifluoropropyl)-3,4-dihydro-2H-1-benzopyran were obtained in oil form.

$[\alpha]_D^{20}$=−87.1° (c=1; dichloromethane).

4.8. 6-Ethoxycarbonylamino-2(S)-(3,3,3-trifluoropropyl)-3,4-dihydro-2H-1-benzopyran 3.2 g (13 mmol) of 6-amino-2(S)-(3,3,3-trifluoropropyl)-3,4-dihydro-2H-1-benzopyran are treated under conditions analogous to those of step 6 of Example 1. 4.1 g of product are obtained.

Melting point: 90° C. $[\alpha]_D^{20}$=+67.4° (c=1; dichloromethane).

According to the same process, starting from 2.5 g (10 mmol) of 6-amino-2(R)-(3,3,3-trifluoropropyl)-3,4-dihydro-2H-1-benzopyran, 3.2 g of 6-ethoxycarbonylamino-2(R)-(3,3,3-trifluoropropyl)-3,4-dihydro-2H-1-benzopyran were obtained.

Melting point: 88° C. $[\alpha]_D^{20}$=−77.4° (c=1; dichloromethane).

4.9. 3-[2(S)-(3,3,3-Trifluoropropyl)-3,4-dihydro-2H-1-benzopyran-6-yl]-5(R)-methoxymethyloxazolidin-2-one 2.3 g (10 mmol) of 6-ethoxycarbonylamino-2(S)-(3,3,3-trifluoropropyl)-3,4-dihydro-2H-1-benzopyran are treated with 4(S)-methoxymethyl-1,3-dioxolan-2-one under conditions analogous to those of step 7 of Example 1. 1.6 g of product are obtained.

Melting point: 116.0–116.1° C. $[\alpha]_D^{20}$=+37.4° (c=1; dichloromethane).

According to the same process, starting from 1.5 g (4.7 mmol) of 6-ethoxycarbonylamino-2(R)-(3,3,3-trifluoropropyl)-3,4-dihydro-2H-1-benzopyran, 0.65 g of 3-[2(R)-(3,3,3-trifluoropropyl)-3,4-dihydro-2H-1-benzopyran-6-yl]-5(R)-methoxymethyloxazolidin-2-one was obtained.

Melting point: 109.4° C. $[\alpha]_D^{20}$=−107.4° (c=1; dichloromethane).

EXAMPLE 5

3-[2-(3,3,3-trifluoropropyl)-3,4-dihydro-2H-1-benzopyran-6-yl]-5(S)-methoxymethyloxazolidin-2-one 5.1. 4(R)-methoxymethyl-2,2-dimethyl-1,3-dioxolane Into a 6 liter reactor equipped with a condenser, a temperature probe and a dropping funnel are introduced 420 ml of demineralized water and 420 g (10.5 mol) of sodium hydroxide pellets. To the solution, stirred at 20° C., are added 2.3 l of dichloromethane, 396 g (3.00 mol) of (R)-2,2-dimethyl-1,3-dioxolane-4-methanol ($[\alpha]_D^{20}$=−11°; c=4; methanol) and 20.5 g (0.090 mol) of benzyltriethylammonium chloride. 567 g (4.50 mol) of dimethyl sulfate are then added in the course of 50 min, while keeping the temperature below 30° C. The mixture is stirred for 18 hours and then 1 liter of water is added. The organic phase is separated and washed with 0.5 l of water. The aqueous phases are reextracted with 3 l of dichloromethane and then the organic phases are combined, filtered and concentrated by distillation under reduced pressure. 496 g of product are obtained.

5.2. 3(S)-Methoxypropane-1,2-diol

A mixture of 496 g of product obtained in the preceding step is heated to 60° C., with stirring, in 220 ml of demineralized water, then 1.5 ml of 36% hydrochloric acid are added. The heating is maintained for 40 min, then the medium is brought to pH 8–9 by addition of 19 ml of triethylamine. The solvent is evaporated under a pressure of 5.2 kPa, at a temperature below 70° C., then the residue is distilled at 61° C. under a pressure of 13 Pa. 246 g of product are obtained.

$[\alpha]_D^{20}$=+5.8° (c=4; methanol).

5.3. 4(R)-Methoxymethyl-1,3-dioxolan-2-one

Into a round-bottomed flask equipped with a dropping funnel and a distillation assembly are introduced 245 g (3.31 mol) of 3(S)-methoxypropane-1,2-diol and 560 ml (4.62 mol) of diethyl carbonate. The mixture is heated to 95° C. and then a solution of sodium methoxide obtained starting from 10 ml of methanol and 0.5 g (0.02 mol) of sodium is added. The ethanol formed in the course of the reaction is distilled for 2 hours (bottom temperature: 95 to 112° C.; column temperature: 82 to 78° C.), then the mixture is cooled and distilled under a pressure of 13 Pa to separate the excess of diethyl carbonate. 267 g of product are obtained.

$[\alpha]_D^{20}$=+30.3° (c=1; dichloromethane).

5.4. 2-(3,3,3-Trifluoropropyl)-3,4-dihydro-2H-1-benzopyran

Starting from 12.5 g (51 mmol) of 2-(2-hydroxy-3,3,3-trifluoropropyl)-3,4-dihydro-2H-1-benzopyran obtained in step 2 of Example 1, treated under conditions analogous to those of Example 3, 5.4 g of 2-(3,3,3-trifluoropropyl)-3,4-dihydro-2H-1-benzopyran were obtained in oil form.

5.5. 6-Nitro-2-(3,3,3-trifluoropropyl)-3,4-dihydro-2H-1-benzopyran

Starting from 7.0 g of 2-(3,3,3-trifluoropropyl)-3,4-dihydro-2H-1-benzopyran treated under conditions analogous to those of step 3 of Example 1, 4.1 g of 6-nitro-2-(3,3,3-trifluoropropyl)-3,4-dihydro-2H-1-benzopyran were obtained in oil form.

5.6. 6-Amino-2-(3,3,3-trifluoropropyl)-3,4-dihydro-2H-1-benzopyran

Starting from 4.1 g (15 mmol) of 6-nitro-2-(3,3,3-trifluoropropyl)-3,4-dihydro-2H-1-benzopyran treated under conditions analogous to those of step 7 of Example 4, 2.3 g of 6-amino-2-(3,3,3-trifluoropropyl)-3,4-dihydro-2H-1-benzopyran were obtained in oil form.

5.7. 6-Ethoxycarbonylamino-2-(3,3,3-trifluoropropyl)-3,4-dihydro-2H-1-benzopyran Starting from 2.2 g (9 mmol) of 6-amino-2-(3,3,3-trifluoropropyl)-3,4-dihydro-2H-1-benzopyran treated under conditions analogous to those of step 6 of Example 1, 2.8 g of 6-ethoxycarbonylamino-2-(3,3,3-trifluoropropyl)-3,4-dihydro-2H-1-benzopyran were obtained.

Melting point: 88° C.

5.8. 3-[2-(3,3,3-Trifluoropropyl)-3,4-dihydro-2H-1-benzopyran-6-yl]-5(S)-methoxymethyloxazolidin-2-one 1.3 g (4.1 mmol) of 6-ethoxycarbonylamino-2-(3,3,3-trifluoropropyl)-3,4-dihydro-2H-1-benzopyran are treated with 4(R)-methoxymethyl-1,3-dioxolan-2-one under conditions analogous to those of step 7 of Example 1. After recrystallization in a mixture of diethyl ether and diisopropyl ether, 0.67 g of product is obtained.

Melting point: 115.5–115.7° C. $[\alpha]_D^{20}$=+36.9° (c=1; dichloromethane).

EXAMPLE 6

3-[2(S)-(3,3,3-trifluoropropyl)-3,4-dihydro-2H-1-benzopyran-6-yl]-5(R)-hydroxymethyloxazolidin-2-one To a solution of 0.80 g (2.2 mmol) of 3-[2(S)-(3,3,3-trifluoropropyl)-3,4-dihydro-2H-1-benzopyran-6-yl]-5(R)-methoxymethyloxazolidin-2-one in 30 ml of dichloromethane are added dropwise, at −5° C., 4.4 ml (4.4 mmol) of a 1M solution of boron tribromide in dichloromethane. The mixture is stirred at 0° C. for 3 hours, then hydrolyzed by adding ammonia until the pH is basic. The product is then extracted with dichloromethane, and the organic phase is washed with water, dried over sodium sulfate and concentrated under reduced pressure. By chromatography of the residue on a silica column using a 2% solution of methanol in dichloromethane and trituration of the product obtained in ethanol, 0.29 g of product is obtained.

Melting point: 134.9–135.0° C. $[\alpha]_D^{20}$=+38.4° (c=1; dimethyl sulfoxide).

EXAMPLE 7

3-[2-cyanoethyl-3,4-dihydro-2H-1-benzopyran-6-yl]-5(R)-methoxymethyloxazolidin-2-one 7.1. Ethyl (3,4-dihydro-2H-1-benzopyranylidene)-2-acetate To a solution of 42.5 g (287 mmol) of dihydrocoumarin in 500 ml of chloroform are added 123 g (287 mmol) of carbethoxymethyltriphenylphosphorane. The mixture is heated to reflux for 3 days, then the solvent is evaporated under reduced pressure and the oil obtained is chromatographed on a silica column using a 50/50 mixture of dichloromethane and cyclohexane. 44 g of a mixture of cis and trans isomers are obtained in oil form.

7.2. Ethyl 3,4-dihydro-2H-1-benzopyran-2-acetate

A solution of 44 g of the mixture of isomers obtained in the preceding step is hydrogenated for 4 days in 400 ml of ethanol, in the presence of 10 g of 10% palladium on carbon containing 50% of water and 1.5 ml of hydrochloric ethanol. The reaction mixture is then filtered and concentrated under reduced pressure. By chromatography of the residue on a silica column using a 5% mixture of ethyl acetate in cyclohexane, 12 g of product are obtained in oil form.

7.3. 2-(3,4-Dihydro-2H-1-benzopyran)-2-ethanol

To a suspension of 2.1 g (54 mmol) of lithium aluminum hydride in 80 ml of diethyl ether is added dropwise, at 0° C., a solution of 12 g (54 mmol) of ethyl 3,4-dihydro-2H-1-benzopyran-2-acetate in 80 ml of diethyl ether. The mixture is stirred for 2 hours at 0° C., then the excess hydride is hydrolyzed with moist sodium sulfate. After filtration, the organic phase is dried over sodium sulfate and concentrated under reduced pressure. 9 g of product are obtained in oil form.

7.4. 2-p-Toluenesulfonyloxyethyl-3,4-dihydro-2H-1-benzopyran

To a solution of 9.0 g (51 mmol) of 2-(3,4-dihydro-2H-1-benzopyran)-2-ethanol, 8 ml (99 mmol) of pyridine and 80 mg of dimethylaminopyridine in 50 ml of dichloromethane is added, dropwise, a solution of 10.1 g (53 mmol) of p-toluenesulfonyl chloride in 50 ml of dichloromethane. The mixture is stirred for 18 hours and then washed with water and the organic phase is dried over sodium sulfate. By chromatography of the residue on a silica column using cyclohexane containing 5 to 10% of ethyl acetate, 12.4 g of product are obtained.

Melting point: 64° C.

7.5. 2-Cyanoethyl-3,4-dihydro-2H-1-benzopyran

A mixture of 15.8 g (47 mmol) of 2-p-toluenesulfonyloxyethyl-3,4-dihydro-2H-1-benzopyran and 3.4 g (52 mmol) of potassium cyanide in 320 ml of dimethyl sulfoxide is stirred for 2 hours. After addition of water, the product is extracted with chloroform containing a little methanol and then the organic phase is washed with a saturated solution of sodium chloride, dried over sodium sulfate and concentrated under reduced pressure. By chromatography of the residue on a silica column using cyclohexane containing 10% ethyl acetate, 7.8 g of compound are obtained in oil form.

7.6. 2-Cyanoethyl-6-nitro-3,4-dihydro-2H-1-benzopyran

A solution of 7.7 g (41 mmol) of 2-cyanoethyl-3,4-dihydro-2H-1-benzopyran in 150 ml of trifluoroacetic acid is reacted for 15 min with 10.5 g (123 mmol) of sodium nitrate, and then the mixture is poured into ice water and the product is extracted with dichloromethane. The organic phase is then dried over sodium sulfate and concentrated under reduced pressure. By chromatography of the residue on a silica column using cyclohexane containing 30% ethyl acetate, 4.5 g of product are obtained.

7.7. 2-Cyanoethyl-6-amino-3,4-dihydro-2H-1-benzopyran

A solution of 4.3 g (18.5 mmol) of 2-cyanoethyl-6-nitro-3,4-dihydro-2H-1-benzopyran in 80 ml of tetrahydrofuran is hydrogenated in the presence of 1 g of palladium on 5% barium sulfate. The mixture is stirred for 2 days, then it is filtered and the filtrate is concentrated under reduced pressure. By chromatography of the residue on a silica column using cyclohexane containing 30% ethyl acetate, 2.5 g of product are obtained.

7.8. 2-Cyanoethyl-6-ethoxycarbonylamino-3,4-dihydro-2H-1-benzopyran

By a process analogous to that of step 6 of Example 1, starting from 2.4 g (12 mmol) of 2-cyanoethyl-6-amino-3, 4-dihydro-2H-1-benzopyran, 1.24 ml (13.0 mmol) of ethyl chloroformate and 1.5 g (18 mmol) of sodium hydrogencarbonate, 2.0 g of product are obtained.

7.9. 3-[2-Cyanoethyl-3,4-dihydro-2H-1-benzopyran-6-yl]-5 (R)-methoxymethyloxazolidin-2-one By a process analogous to that of step 7 of Example 1, starting from 1.9 g (6.9 mmol) of 2-cyanoethyl-6-ethoxycarbonylamino-3,4-dihydro-2H-1-benzopyran, 0.1 g (0.7 mmol) of potassium carbonate and 1.2 g (0.9 mmol) of 4(S)-methoxymethyl-1,3-dioxolan-2-one, 0.6 g of product is obtained in oil form.

$[\alpha]_D^{20}$=−30.0° (c=1; dichloromethane).

EXAMPLE 8

3-[2-cyanoethyl-2,3-dihydrobenzofuran-5-yl]-5(R)-methoxymethyloxazolidin-2-one 8.1. 2-Cyanoethyl-2,3-dihydrobenzofuran Starting from 15.2 g (48 mmol) of 2-p-toluenesulfonyloxyethyl-2,3-dihydrobenzofuran (compound described in the U.S. Pat. No. 4,129,655) and 3.4 g (52 mmol) of potassium cyanide in 170 ml of dimethyl sulfoxide treated under the conditions described in step 5 of Example 7, 7.7 g of product were obtained in oil form.

8.2. 2-Cyanoethyl-5-nitro-2,3-dihydrobenzofuran

Starting from 7.5 g (43 mmol) of 2-cyanoethyl-2,3-dihydrobenzofuran in 120 ml of trifluoroacetic acid and 11 g (130 mmol) of sodium nitrate treated under the conditions described in step 6 of Example 7, 3.4 g of product were obtained.

8.3. 5-Amino-2-cyanoethyl-2,3-dihydrobenzofuran

Starting from 3.2 g (15 mmol) of 2-cyanoethyl-5-nitro-2,3-dihydrobenzofuran in 80 ml of tetrahydrofuran, hydrogenated in the presence of 0.32 g of palladium on 5% barium sulfate under the conditions described in step 7 of Example 7, 2.7 g of product were obtained.

8.4. 2-Cyanoethyl-5-ethoxycarbonylamino-2,3-dihydrobenzofuran

Starting from 2.6 g (14 mmol) of 5-amino-2-cyanoethyl-2,3-dihydrobenzofuran, 1.45 ml (15.2 mmol) of ethyl chloroformate and 1.7 g (21 mmol) of sodium hydrogencarbonate treated under the conditions described in step 6 of Example 1, 3.2 g of product were obtained.

8.5. 3-[2-Cyanoethyl-2,3-dihydrobenzofuran-5-yl]-5-(R)-methoxymethyloxazolidin-2-one By a process analogous to that of step 7 of Example 1, starting from 3.0 g (12 mmol) of 2-cyanoethyl-5-ethoxycarbonylamino-2,3-dihydrobenzofuran, 0.16 g (1.2 mmol) of potassium carbonate and 4 g (30 mmol) of 4(S)-methoxymethyl-1,3-dioxolan-2-one, 0.55 g of product was obtained in oil form.

$[\alpha]_D^{20}$=−31.0° (c=1; dichloromethane)

EXAMPLE 9

3-[2-propyl-3,4-dihydro-2H-1-benzopyran-6-yl]-5 (R)-methoxymethyloxazolidin-2-one 9.1. 2-Acetylphenyl butyrate A mixture of 50 g (367 mmol) of 2-hydroxyacetophenone and 47 g (440 mmol) of butyryl chloride in 100 ml of pyridine is stirred for 30 minutes, then diluted with diethyl ether and washed successively with water and aqueous hydrochloric acid. The organic phase is then dried over sodium sulfate, concentrated under reduced pressure and coevaporated 3 times with toluene. By chromatography of the residue on a silica column using a 0–30% mixture of ethyl acetate in cyclohexane, 72 g of product are obtained in oil form.

9.2. 2-Propyl-1-benzopyran-4-one

A mixture of 72 g (350 mmol) of 2-acetylphenyl butyrate in 350 ml of pyridine and 31 g (560 mmol) of potassium hydroxide is stirred for 1 hour at 50° C. The reaction medium is then cooled, diluted with diethyl ether and washed with water and then with aqueous hydrochloric acid. The organic phase is then dried, concentrated under reduced pressure and coevaporated 3 times with toluene. The product formed is dissolved in a mixture of 490 ml of acetic acid and 20 ml of concentrated hydrochloric acid, heated for 1 hour, and then the medium is cooled, diluted with diethyl ether, washed with water, dried over sodium sulfate and concentrated under reduced pressure. By chromatography of the residue on a silica column with a 0–20% mixture of ethyl acetate in cyclohexane, 44 g of product are obtained in oil form.

9.3. 2-Propyl-3,4-dihydro-2H-1-benzopyran

A solution of 44 g (234 mmol) of 2-propyl-1-benzopyran-4-one in 350 ml of ethanol and 125 ml of concentrated hydrochloric acid is hydrogenated for 8 hours under a pressure of 500 kPa, in the presence of 14 g of 10% palladium on carbon containing 50% of water. The mixture is then filtered and the filtrate is concentrated under reduced pressure. By chromatography of the residue on a silica column using dichloromethane, 26 g of product are obtained in oil form.

9.4. 6-Nitro-2-propyl-3,4-dihydro-2H-1-benzopyran 8.0 g (45 mmol) of 2-propyl-3,4-dihydro-2H-1-benzopyran are treated under conditions analogous to those of step 3 of Example 1. 5.7 g of product are obtained in oil form.

9.5. 6-Amino-2-propyl-3,4-dihydro-2H-1-benzopyran 5.7 g (26 mmol) of 6-nitro-2-propyl-3,4-dihydro-2H-1-benzopyran are treated under conditions analogous to those of step 5 of Example 1. 3.6 g of product are obtained in oil form.

9.6. 6-Ethoxycarbonylamino-2-propyl-3,4-dihydro-2H-1-benzopyran 3.5 g (18 mmol) of 6-amino-2-propyl-3,4-dihydro-2H-1-benzopyran are treated under conditions analogous to those of step 6 of Example 1. 3.4 g of product are obtained.

Melting point: 94° C.

9.7. 3-[2-Propyl-3,4-dihydro-2H-1-benzopyran-6-yl]-5(R)-methoxymethyloxazolidin-2-one 3.3 g (13 mmol) of 6-ethoxycarbonylamino-2-propyl-3,4-dihydro-2H-1-benzopyran are treated with 4(S)-methoxymethyl-1,3-dioxolan-2-one under conditions analogous to those of step 7 of Example 1. After recrystallization in a mixture of diisopropyl ether and petroleum ether, 0.67 g of product is obtained.

Melting point: 78.5–78.7° C. $[\alpha]_D^{20}$=−38.6° (c=1; dichloromethane).

EXAMPLE 10

3-[2-(3,3,3-trifluoropropyl)-2,3-dihydrobenzofuran-5-yl]-5(R)-methoxymethyloxazolidin-2-one

10.1. 2-(3,3,3-Trifluoropropyl)-5-nitrobenzofuran

A suspension of 4.0 g (8.1 mmol) of (2-hydroxy-5-nitrophenyl)methyltriphenylphosphonium bromide (compound described in Chem. Ber. 1986, 119, 2169) is heated to reflux in 50 ml of toluene, then 5.1 ml (36 mmol) of triethylamine and 1.9 g (12 mmol) of 4,4,4-trifluorobuteryl chloride are added. The mixture is stirred for 2 hours, then it is filtered and the filtrate is concentrated under reduced pressure. By chromatography of the residue on a silica column using a 0–30% mixture of dichloromethane in cyclohexane, 1.1 g of product are obtained.

Melting point: 70–71° C.

10.2. 5-Amino-2-(3,3,3-trifluoropropyl)benzofuran

A mixture of 2.4 g (9.2 mmol) of 2-(3,3,3-trifluoropropyl)-5-nitrobenzofuran, 0.65 g (17 mmol) of sodium borohydride, 45 mg of Adogen 464 and 0.38 g of 10% palladium on carbon containing 50% of water is stirred for 5 hours in 95 ml of dichloromethane and 48 ml of water, then it is filtered on silica and the silica is rinsed with ethanol. The filtrate is then concentrated under reduced pressure and coevaporated with toluene. After chromatography of the residue on a silica column using a 0–30% mixture of ethyl acetate in cyclohexane, 2.0 g of product are obtained.

Melting point: 74° C.

10.3. 5-Ethoxycarbonylamino-2-(3,3,3-trifluoropropyl)-benzofuran

A solution of 2.0 g (8.7 mmol) of 5-amino-2-(3,3,3-trifluoropropyl)benzofuran in 30 ml of a 9/1 mixture of tetrahydrofuran and water is reacted for 30 minutes with 0.92 ml (9.6 mmol) of ethyl chloroformate in the presence of 1.1 g (13 mmol) of sodium hydrogen-carbonate. The reaction medium is then diluted with water and dichloromethane, then the organic phase is separated, dried over sodium sulfate and concentrated under reduced pressure. 2.5 g of product are obtained.

Melting point: 108° C.

10.4. 3-[2-(3,3,3-Trifluoropropyl)benzofuran-5-yl]-5(R)-methoxymethyloxazolidin-2-one A solution of 1.2 g (4.0 mmol) of 5-ethoxycarbonylamino-2-(3,3,3-trifluoropropyl)benzofuran in 16 ml of dimethylformamide is stirred at 140° C. for 4 hours in the presence of 55 mg (0.40 mmol) of potassium carbonate and 700 mg (5.2 mmol) of 4(S)-methoxymethyl-1,3-dioxolan-2-one added by fractions. The reaction mixture is then poured into water, the product is extracted with diethyl ether, and the organic phase is dried over sodium sulfate and concentrated under reduced pressure. By chromatography of the oil obtained on a silica column using a 0–30% mixture of ethyl acetate in cyclohexane and recrystallization of the residue in a mixture of diisopropyl ether and diethyl ether, 1.05 g of product are obtained.

Melting point: 79.9–80.0° C. $[\alpha]_D^{20}$=−36.9 (c=1; dichloromethane).

10.5. 3-[2-(3,3,3-Trifluoropropyl)-2,3-dihydrobenzofuran-5-yl]-5(R)-methoxymethyloxazolidin-2-one A solution of 0.60 g (1.7 mmol) of 3-[2-(3,3,3-trifluoropropyl)benzofuran-5-yl]-5(R)-methoxymethyloxazolidin-2-one in 40 ml of ethanol is hydrogenated for 17 hours in the presence of 1 ml of hydrochloric ethanol and 0.3 g of 10% palladium on carbon containing 50% of water. The mixture is then filtered and the solvent is evaporated under reduced pressure. By chromatography of the residue on a silica column using a 2% mixture of methanol in dichloromethane and recrystallization in diisopropyl ether, 0.55 g of product is obtained.

Melting point=89.1–89.4° C. $[\alpha]_D^{20}$=−16.8° C. (c=1; dichloromethane).

EXAMPLE 11

3-[2-(3,3,3-trifluoropropyl)-2,3-dihydrobenzofuran-5-yl]-5(R)-hydroxymethyloxazolidin-2-one To a solution of 0.20 g (0.58 mmol) of 3-[2-(3,3,3-trifluoropropyl)-2,3-dihydrobenzofuran-5-yl]-5(R)-methoxymethyloxazolidin-2-one in 10 ml of dichloromethane is added dropwise, at −5° C., 1.0 ml (1.0 mmol) of a 1M solution of boron tribromide in dichloromethane. The mixture is stirred at 0° C. for 1 hour, then it is hydrolyzed by adding ammonia until the pH is basic. The product is then extracted with dichloromethane, and the organic phase is washed with water, dried over sodium sulfate and concentrated under reduced pressure. By chromatography of the residue on a silica column using a 1% mixture of methanol in dichloromethane and trituration of the product obtained in a mixture of diethyl ether and petroleum ether, 93 mg of product are obtained.

Melting point=93.5–94.0° C. $[\alpha]_D^{20}$=−21° (c=1; dimethyl sulfoxide).

The compounds of the invention are compiled in the following table with their physical characteristics.

TABLE (I)

| No. | $R_1$ | $R_2$ | $R_3$ | n | config. | M.P. (° C.) | $[\alpha]_D^{20}$ (c = 1) | solvent |
|---|---|---|---|---|---|---|---|---|
| 1a | $CF_3$ | OH | $CH_3$ | 1 | 5(R), 2(R,S) | 133–134 | — | — |
| 1b |  |  |  |  |  | 81–83 | — | — |
| 2 | $CF_3$ | OH | H | 1 | 5(R), 2(R,S) | 123.7–123.8 | −31.8 | dimethyl sulfoxide |
| 3 | $CF_3$ | H | $CH_3$ | 1 | 5(R), 2(R,S) | 110–111 | — | — |
| 4 | $CF_3$ | H | $CH_3$ | 1 | 5(R), 2(S) | 116.0–116.1 | +37.4 | dichloromethane |
| 5 | $CF_3$ | H | $CH_3$ | 1 | 5(R), 2(R) | 109.4 | −107.4 | dichloromethane |
| 6 | $CF_3$ | H | $CH_3$ | 1 | 5(S), 2(R,S) | 115.5–115.7 | +36.9 | dichloromethane |
| 7 | $CF_3$ | H | H | 1 | 5(R), 2(S) | 134.9–135.0 | +38.4 | dimethyl sulfoxide |
| 8 | CN | H | $CH_3$ | 1 | 5(R), 2(R,S) | oil | −30.0 | dichloromethane |
| 9 | $CH_3$ | H | $CH_3$ | 1 | 5(R), 2(R,S) | 78.5–78.7 | −38.6 | dichloromethane |
| 10 | CN | H | $CH_3$ | 0 | 5(R), 2(R,S) | oil | −31.0 | dichloromethane |
| 11 | $CF_3$ | H | $CH_3$ | 0 | 5(R), 2(R,S) | 89.1–89.4 | −16.8 | dichloromethane |
| 12 | $CF_3$ | H | $CH_3$ | 0 | 5(S), 2(R,S) | 86.4–88.0 | +23.1 | dichloromethane |
| 13 | $CF_3$ | H | H | 0 | 5(R), 2(R,S) | 93.5–94.0 | −21.0 | dimethyl sulfoxide |

The compounds of the invention were the subjects of pharmacological tests allowing their inhibitory power on monoamine oxidase A and monoamine oxidase B to be determined.

The measurements of the MAO-A and MAO-B activities in vitro were carried out using a rat brain homogenate as an enzyme source, according to the method described by C. Fowler and M. Strolin-Benedetti, in J. Neurochem., 40, 1534–1541 (1983).

The standard determination consists in homogenizing the rat brain in 20 volumes of 0.1M phosphate buffer (pH=7.4) and in preincubating 100 µl of homogenate (5 mg of tissue) at 37° C. for 20 minutes, in the absence or in the presence of different inhibitor concentrations studied. The reaction is started by the addition of [$^{14}$C] serotonin ([$^{14}$C]5HT, final concentration 125 µM) for the measurement of the activity of the MAO-A or of [$^{14}$C]phenylethylamine ([$^{14}$C]PEA, final concentration 8 µM) for the measurement of the MAO-B activity, in a final volume of 500 µl. After incubating the [$^{14}$C]5HT for 5 minutes and the [$^{14}$C]PEA for 1 minute, the reaction is stopped by addition of 200 µl of 4N hydrochloric acid. The radioactive metabolites from the oxidative deamination are then separated from the nontransformed substrate by organic phase extraction, and quantified by counting the radioactivity.

The inhibitory activities with respect to the MAO-A and the MAO-B are given respectively by the inhibition constants Ki (MAO-A) and Ki (MAO-B).

For the compounds of the invention, the Ki (MAO-A) vary between 1.5 and 17.7 nM, the Ki (MAO-B) generally being greater than 1000 nM.

The results obtained show that the compounds of the invention can be used for the preparation of selective inhibitory drugs for MAO-A, these drugs finding employment in therapeutics, especially in the treatment of depressive states, panic attacks, phobias, anxiety, cognitive deficits connected with age, with dementias or with cerebrovascular or traumatic accidents, and in the prevention and the treatment of neurodegenerative illnesses of the central nervous system such as Parkinson's disease and Alzheimer's disease, dependence and withdrawal treatment connected with the consumption of alcohol, or tobacco and/or of intoxicants, and loss of appetite.

The compounds of the invention can be present, in association with at least one excipient, in the form of pharmaceutical compositions formulated with a view to administration, especially by the oral, parenteral or rectal route, for example in the form of tablets, coated tablets, capsules, solutions, suspensions or suppositories.

By the oral, parenteral and rectal routes, the dose of active principle administered per day can vary between 1 and 100 mg/kg, in one or more administrations.

Annex 1
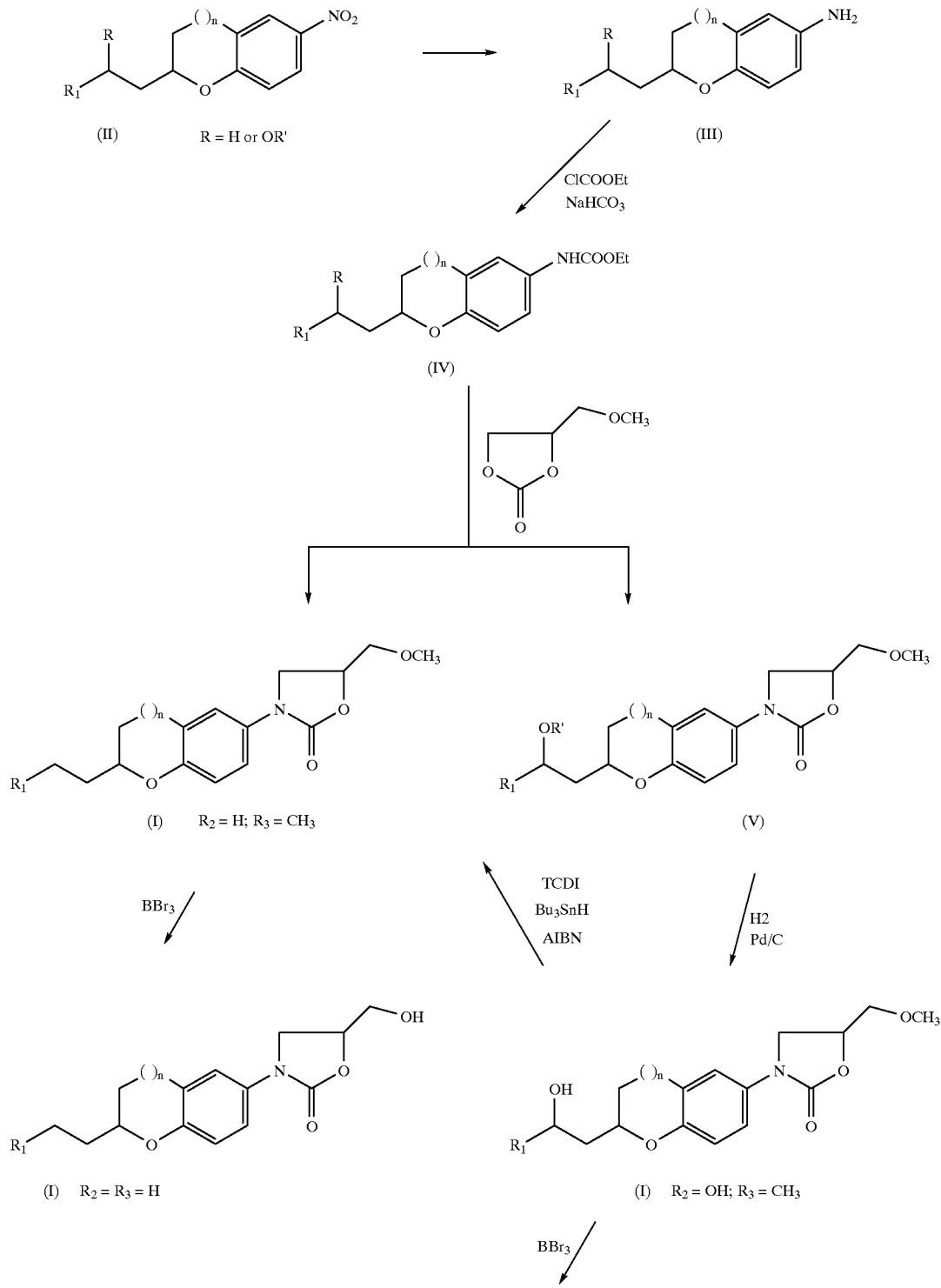

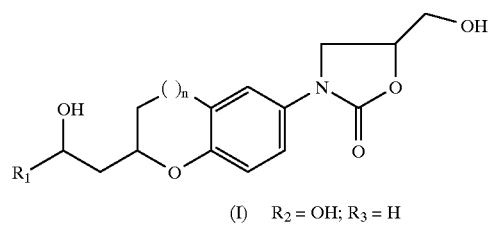
(I)   R$_2$ = OH; R$_3$ = H
Annex 2
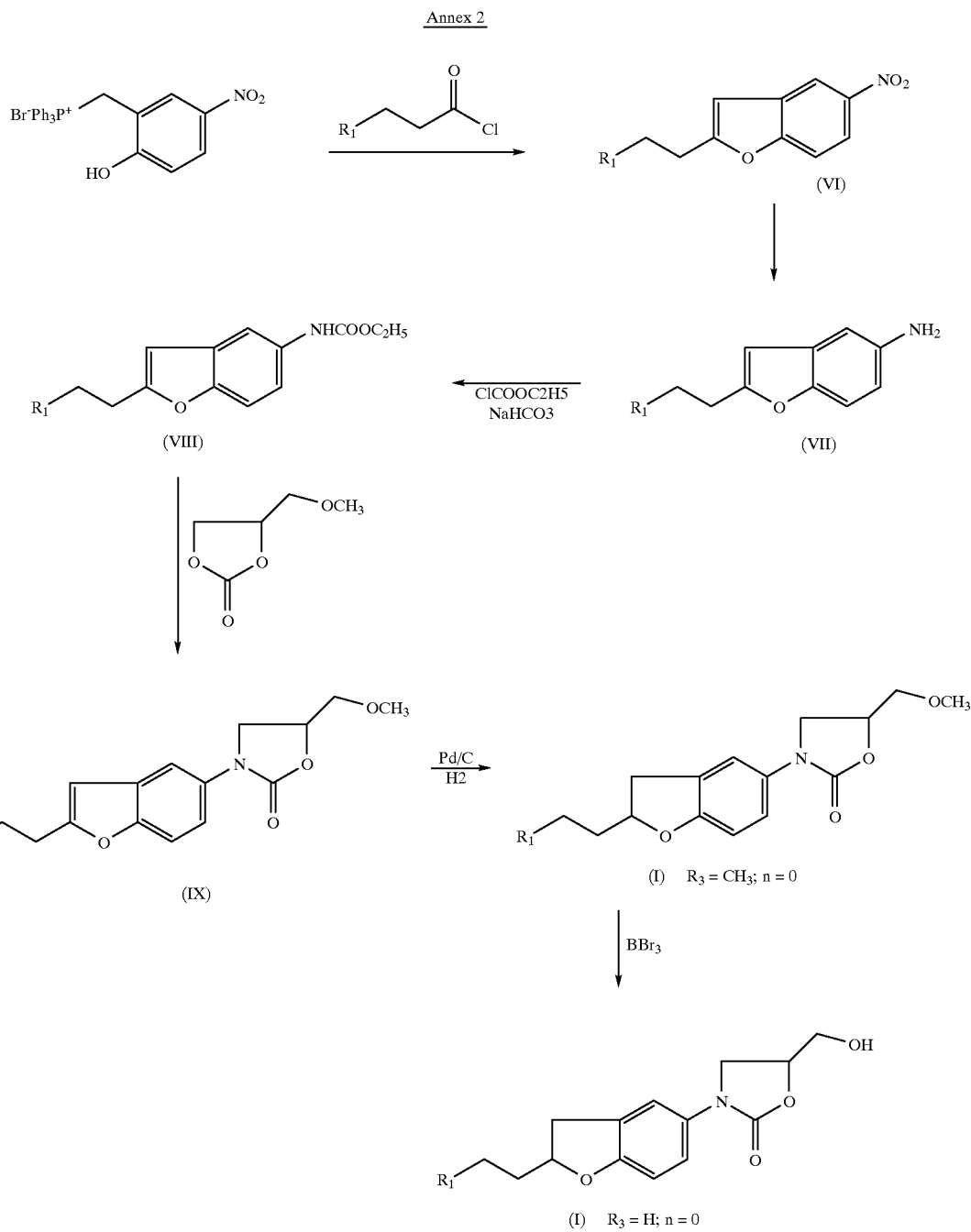

Annex 3
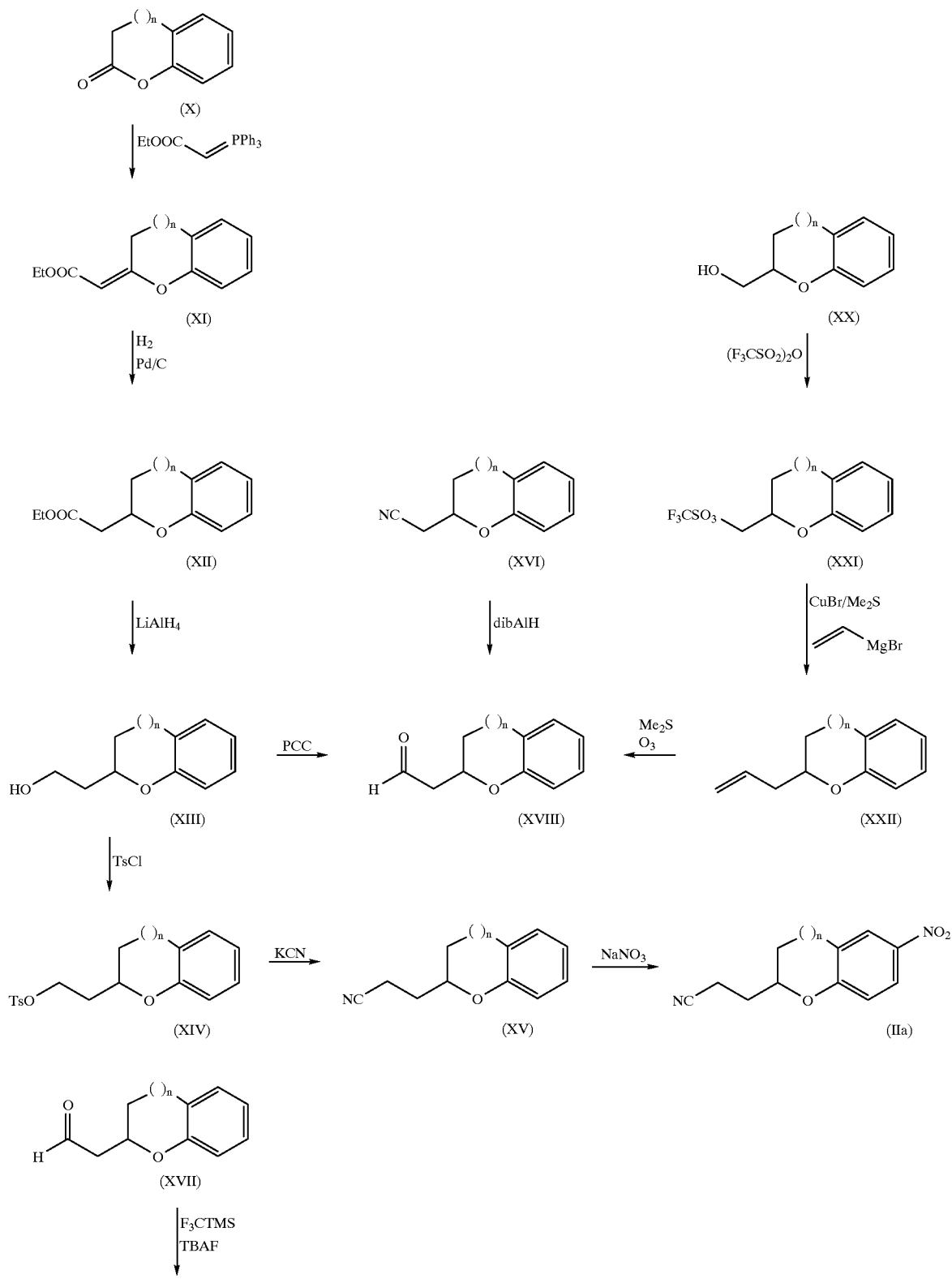

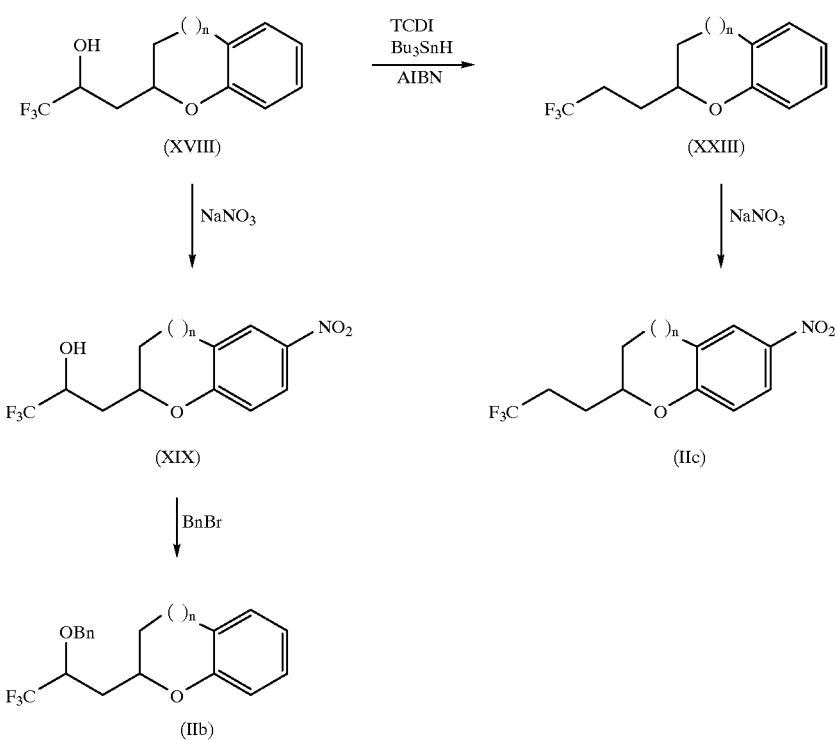
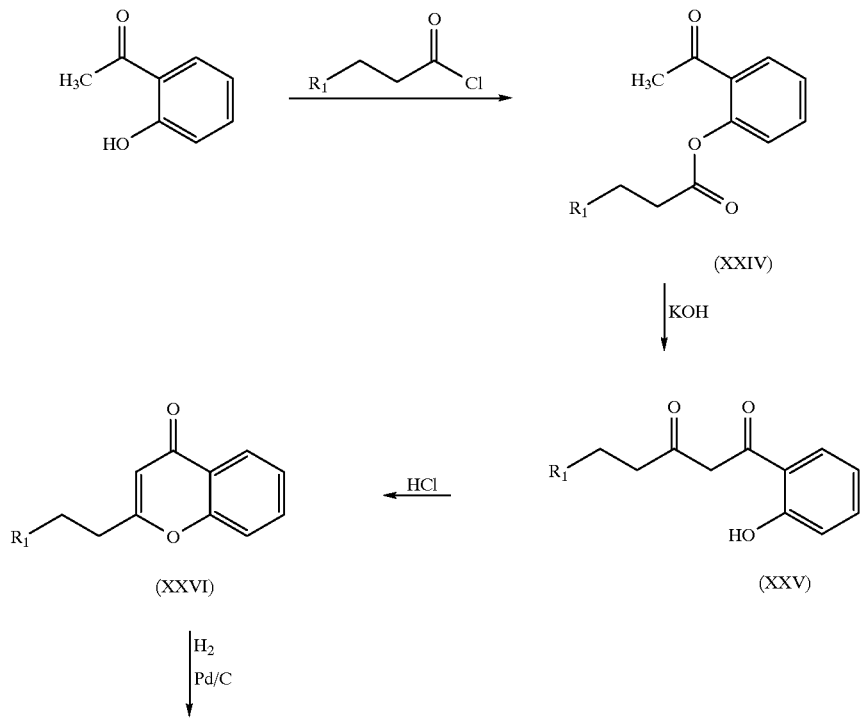
Annex 4

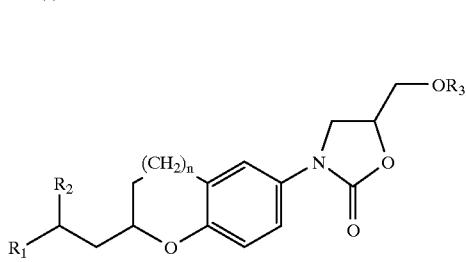

We claim:

1. A compound derived from oxazolidin-2-one, of general formula (I)

(I)

in which:
n is equal to 0 or 1,
$R_1$ represents a cyano group, an alkyl group comprising 1 to 4 carbon atoms or a fluoroalkyl group comprising 1 to 4 carbon atoms,
$R_2$ represents a hydrogen atom or a hydroxyl group, and
$R_3$ represents a hydrogen atom or a methyl group, in the form of enantiomers or of diastereoisomers or of mixtures of these different forms including racemic mixtures.

2. A compound as claimed in claim 1, wherein $R_3$ represents a methyl group.

3. A compound as claimed in claim 1, wherein $R_1$ represents a cyano, methyl or trifluoromethyl group.

4. 3-[2-(3,3,3-Trifluoropropyl)-3,4-dihydro-2H-1-benzopyran-6-yl]-5-methoxymethyloxazolidin-2-one, its enantiomers and diastereoisomers.

5. 3-[2-Propyl-3,4-dihydro-2H-1-benzopyran-6-yl]-5-methoxymethyloxazolidin-2-one, its enantiomers and diastereoisomers.

6. 3-[2-(3,3,3-Trifluoropropyl)-2,3-dihydro-benzofuran-5-yl]-5-methoxymethyloxazolidin-2-one, its enantiomers and diastereoisomers.

7. A process for the preparation of compounds of formula (I) as claimed in claim 1 for which $R_3$ represents a methyl group, which comprises reacting a compound of formula (IV)

(IV)

where $R_1$ has one of the meanings given in claim 1 and R represents either a hydrogen atom or a phenylmethoxy group, with 4-methoxymethyl-1,3-dioxolan-2-one to obtain either a compound of formula (I) in which $R_2$ is a hydrogen atom or a compound of formula (V)

(V)

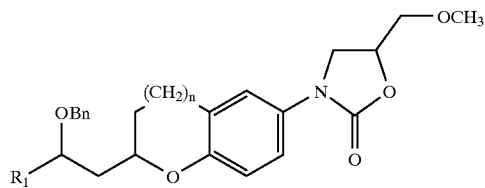

which is deprotected to give a compound of formula (I) in which $R_2$ represents a hydroxyl group, and optionally treated with thiocarbonyldiimidazole and then with tributyltin hydride and α,α'-azodiisobutyronitrile to give a compound of formula (I) in which $R_2$ is a hydrogen atom.

8. A process for the preparation of the compounds as claimed in claim 1 for which $R_3$ represents a hydrogen atom, which comprises treating a corresponding compound of formula (I) where $R_3$ represents a methyl group, with boron tribromide.

9. A pharmaceutical composition which is formed of a compound of formula (I) as claimed in claim 1, in combination with at least one appropriate excipient.

* * * * *